US00PP22902P2

(12) United States Plant Patent
Kivistik

(10) Patent No.: US PP22,902 P2
(45) Date of Patent: Jul. 31, 2012

(54) ***CLEMATIS* PLANT NAMED 'UNAI 008'**

(50) Latin Name: *Clematis patens*
Varietal Denomination: UNAI 008

(76) Inventor: Aili Kivistik, Kose Parish (EE)

( * ) Notice: Subject to any disclaimer, the term of this patent is extended or adjusted under 35 U.S.C. 154(b) by 0 days.

(21) Appl. No.: 12/927,366

(22) Filed: Nov. 12, 2010

(51) Int. Cl.
*A01H 5/00* (2006.01)

(52) U.S. Cl. ..... Plt./228

(58) Field of Classification Search ..... Plt./228
See application file for complete search history.

*Primary Examiner* — Susan McCormick Ewoldt
(74) *Attorney, Agent, or Firm* — Cassandra Bright

(57) ABSTRACT

A new and distinct *Clematis patens* cultivar named 'UNAI 008' is disclosed, characterized by good resistance to normal diseases and pests of *Clematis*, continuous flowering from May through September, with flower buds continuously produced from the leaf axils, large flowers and tepals colored Violet Blue to Violet. Plants are exceptionally floriferous and vigorous. The new cultivar is a *Clematis*, suitable for ornamental garden purposes.

2 Drawing Sheets

Figure 1:
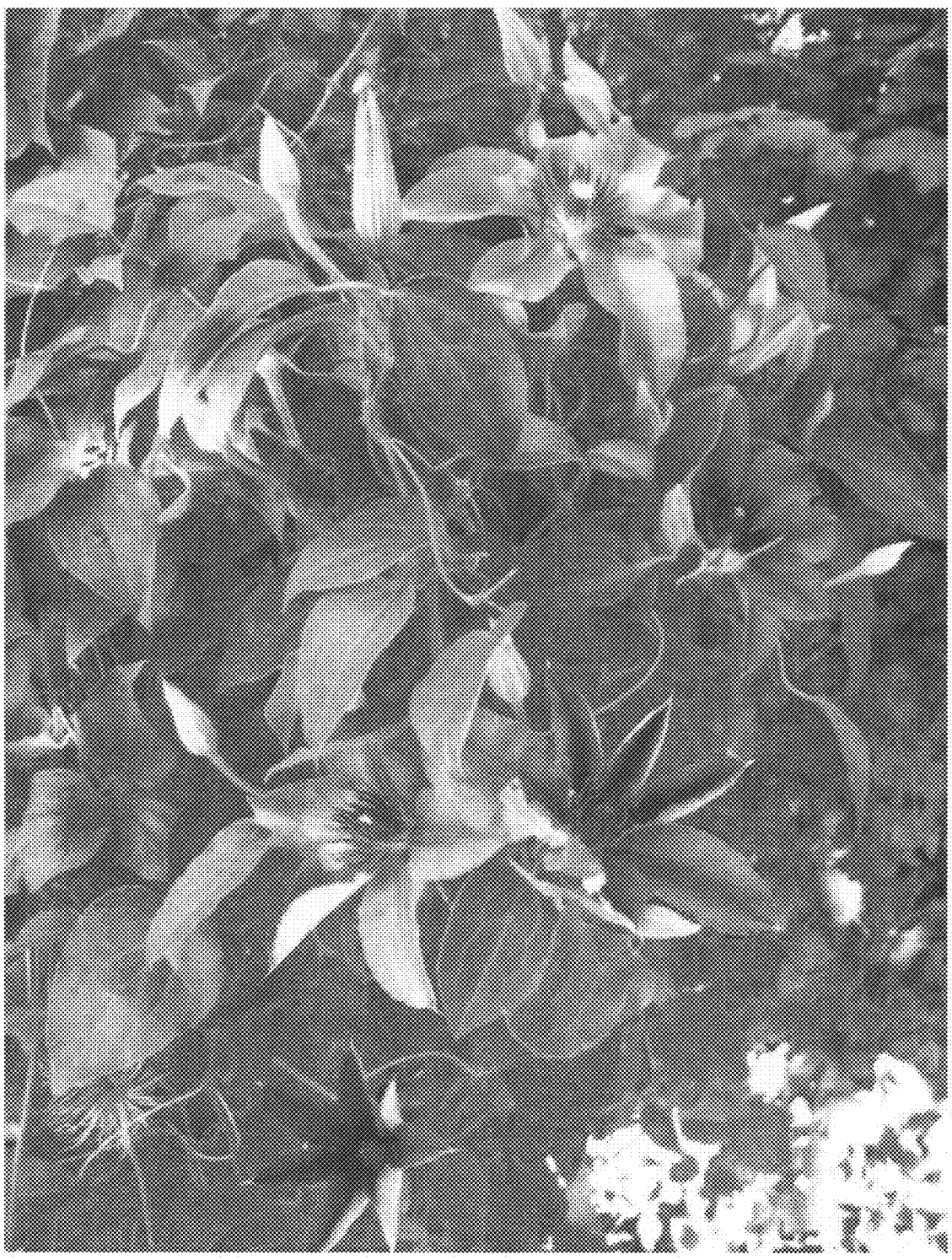

Latin name of the genus and species: *Clematis patens*.
Variety denomination: 'UNAI 008'.

BACKGROUND OF THE INVENTION

The new cultivar is a product of a planned breeding program conducted by the inventor that began in 1978. The objective of the breeding program was to develop *Clematis patens* varieties with abundant, continuous, long season flowering, and plants with a good resistance to diseases and pests typical of *Clematis*. In 1981 the inventor, Aili Kivistik a citizen of Estonia, organized a group of unnamed, unpatented *Clematis patens* varieties for an open pollination breeding project. Seeds originating from this open pollination were planted out, and the new variety was selected in 1986. Specific parents of the new variety are unknown, as the seed was bulk collected, without noting the variety collected from. All work was conducted at a non-commercial nursery in Roogoja, Estonia.

In 1988 the inventor first propagated 'UNAI 008' by vegetative cuttings at the same nursery in Roogoja, Estonia. Subsequent generations have shown that the unique features of this cultivar are stable and reproduced true to type.

SUMMARY OF THE INVENTION

The cultivar 'UNAI 008' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UNAI 008' These characteristics in combination distinguish 'UNAI 008' as a new and distinct *Clematis* cultivar:

1. Good resistance to diseases and pests common to *Clematis*.
2. Continuous flowering from May through September.
3. Very floriferous plants.
4. Flower buds produced continuously from the leaf axils.

5. Very large flowers.
6. Tepal color from Violet to Violet-Blue.

COMPARISON TO KNOWN VARIETIES

Plants of the new cultivar 'UNAI 008' are similar to the known variety of *Clematis patens* 'The President', not patented in most horticultural characteristics, however, plants of the new cultivar 'UNAI 008' flower continuously from May through September, whereas *Clematis patens* 'The President' stops flowering for periods of time. Additionally the 'UNAI 008' has a larger flower.

The new cultivar 'UNAI 008' can also be compared to the known variety *Clematis patens*×*lanuginosa* 'Dorami' U.S. Plant Pat. No. 21,740. Plants are similar in most horticultural characteristics, including the continuous flowering habit, however, plants of the new cultivar produce larger flowers. Flowers of 'Dorami' are typically 10 to 14 cm in diameter whereas 'UNAI 008' plant produce flowers from 16 to 18 cm. Additionally plants of the new cultivar produce flowers of a different shade of Violet, and with a Violet-Blue center bar not produced by plants of 'Dorami'.

The new cultivar 'UNAI 008' can also be compared to the known variety *Clematis patens* 'Zostiwa' U.S. Plant Pat. No. 20,372. Plants are similar in most horticultural characteristics, including similar flower color. However, plants of the new cultivar are more vigorous and spreading than 'Zostiwa'. Additionally the new cultivar begins has larger flowers than 'Zostiwa'.

BRIEF DESCRIPTION OF THE PHOTOGRAPHS

The accompanying photograph in FIG. 1 illustrates in full color a typical flowering plant of 'UNAI 008' grown outdoors in Estonia. The plant is less than one year old.

Figure 2:
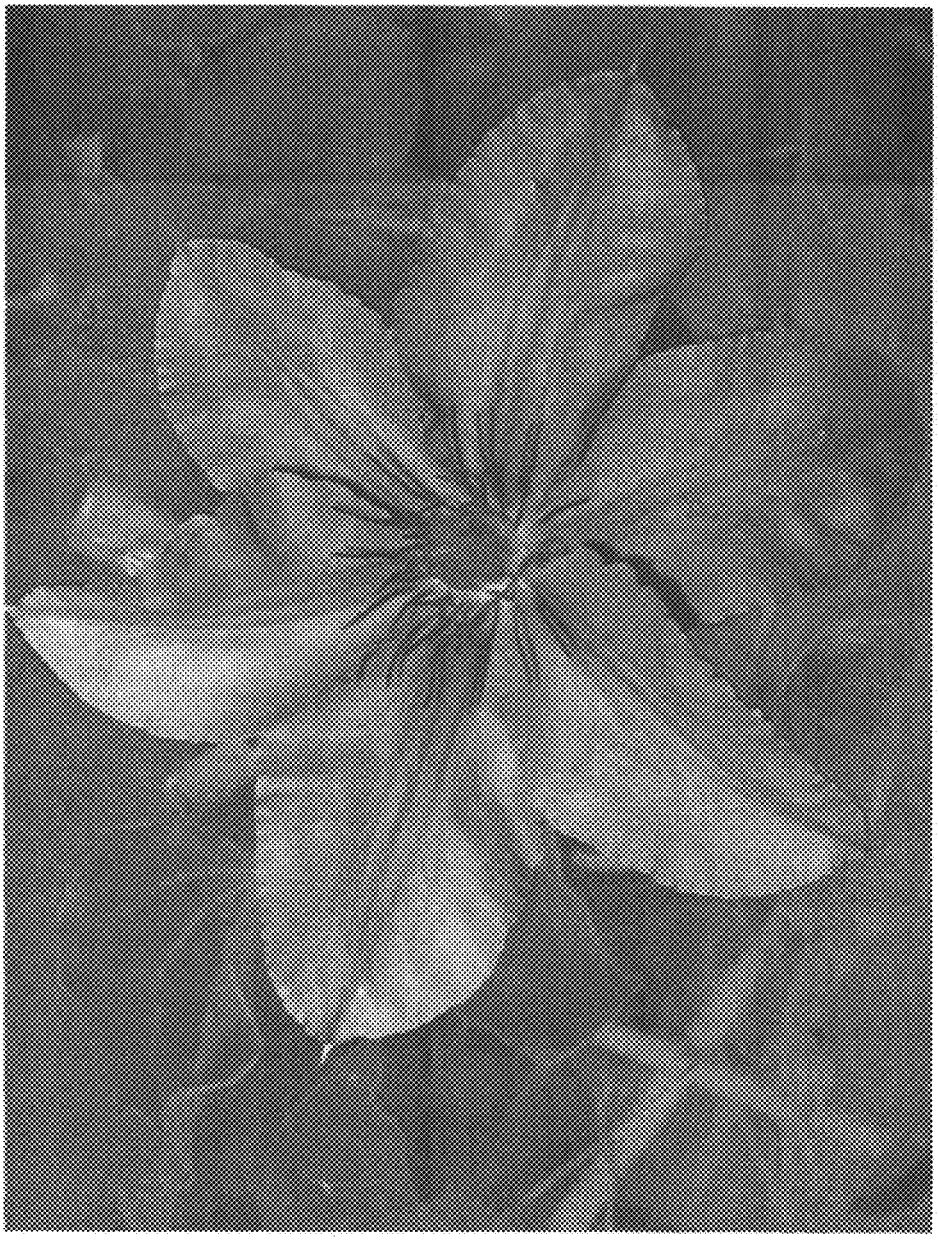

FIG. 2 shows a close up view of a typical flower of 'UNAI 008'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'UNAI 008' plants grown outdoors in Roogoja, Estonia. Plants are approximately 1 year old, in a 1 liter nursery container. The growing conditions are outdoors and unshaded. Temperatures ranged from approximately −2° C. to 20° C. at night to 5° C. to 35° C. during the day. Measurements and numerical values represent averages of typical plant types.

Botanical classification: *Clematis patens* 'UNAI 008'.

PROPAGATION

Time to rooting:

*Initiation*.—Approximately 40 days in the Summer at approximately 25° C.

*Rooted cuttings production*.—Approximately 40 days in the Summer at approximately 25° C.

Root description: Fine, fibrous.

PLANT

Growth habit: Climbing vine.

Height: Approximately 180 cm, measured from the soil line of the pot.

Plant spread: Approximately 150 cm when trained as a vine or when left untrained.

Growth rate: Rapid. During active growing season in Spring, approximately 70 to 100 cm per month.

Branching characteristics: Very well branched, one main branch with at least 10 lateral branches.

Length of main stem: Approximately 180 cm.

Diameter of main stem: Approximately 0.2 to 0.5 cm.

Main stem color: Near RHS Brown 200B.

Main stem texture: Glabrous.

Internode length: Approximately 10 to 15 cm.

Strength: Strong, flexible, semi-woody.

FOLIAGE

Leaf:

*Type*.—Ternate leaves arranged opposite.

Description ternate leaves:

*Leaves per lateral branch*.—Approximately 72 leaflets.

*Average length*.—Approximately 12 cm.

*Average width*.—Approximately 8 cm.

Description leaflets:

*Leaflet petiole*.—Average Length: Approximately 1.0 cm. Color: Near RHS Green 136A. Diameter: Approximately 0.2 cm. Texture: Glabrous.

*Average length*.—Approximate range from 5 to 10 cm.

*Average width*.—Approximate range from 3 to 5 cm.

*Shape of blade*.—Heart, shaped.

*Apex*.—Acute.

*Base*.—Cordate.

*Attachment*.—Petioled.

*Margin*.—Entire.

*Texture of top surface*.—Smooth.

*Texture of bottom surface*.—Smooth.

*Leaf internode length*.—Approximately 1.2 cm.

*Resistance to stress and breakage*.—Very resistant to environmental and mechanical stress.

*Color*.—Young foliage upper side: Near RHS Green 136A. Young foliage under side: Near RHS Green 137D. Mature foliage upper side: Near RHS Green 136A. Mature foliage under side: Near RHS Green 137C.

*Venation*.—Type: Pinnate. Venation color upper side: Near RHS Green 136A. Venation color under side: Near RHS Green 137C.

*Petiole*.—Average Length: Approximate range from 6 to 8 cm. Color: Near RHS Green 136A. Diameter: Approximately 0.2 to 0.3 cm. Texture: Glabrous.

Tendrils not present.

FLOWER

Bloom period:

*Natural season*.—Continuously from approximately May through September.

Flower type and habit: Solitary axillary; flowers facing outward.

Flower longevity on plant: Approximately 5 days, after fully opened. Self-cleaning.

Quantity of flowers: Very free, continuous flowering. Mature plants have at least 50 open flowers during the flowering season.

Flower size:

*Diameter*.—Approximate range from 16 to 18 cm.

*Depth*.—Approximately 1 cm.

Corolla:

*Tepal arrangement*.—Single overlapping whorl.

*Quantity*.—Approximately 6 to 8 per flower.

*Size*.—Length: Approximately 3 cm. Width: Approximately 2 cm.

*Shape*.—Nearly spatulate.

*Margin*.—Entire.

*Apex*.—Acute.

*Base*.—Truncate.

*Aspect*.—Slightly concave, undulation throughout petal blade, very pronounced undulation on margin.

*Texture*.—Smooth, velvety.

Color:

*Tepals*.—When opening: Upper surface: Near RHS Purple-Violet 82A. Lower surface: Near RHS Purple-Violet 82C. Fully opened: Upper surface: Near RHS Violet-Blue 92A with central bar near Violet 88B. Lower surface: Near RHS Violet-Blue 92B with central bar near Violet 85D. Ageing: Upper surface: Near RHS Violet-Blue 92B with central bar near Violet 88C. Lower surface: Near RHS Violet-Blue 92B with central bar near Violet 85D.

Bud:

*Shape*.—Ovate.

*Length*.—Approximately 3 cm.

*Diameter*.—Approximately 1.5 to 2 cm.

*Color*.—Mainly Near RHS Greyed-Green 190D.

Peduncles:

*Length*.—Approximately 0.6 cm.

*Width*.—Approximately 0.3 cm.

*Angle*.—Average 15°.

*Strength.*—Moderate.
*Color.*—Near RHS Green 138A.
Fragrance: None.

REPRODUCTIVE ORGANS

Stamens:
*Number*.—Approximately 60 per flower.
*Anther length.*—1 cm.
*Anther color*.—Near RHS Violet 83A.
*Anther shape*.—Oblong.
*Pollen quantity*.—Moderate.
*Pollen color*.—Near RHS Violet 83B.
*Filament length*.—Approximately 0.2 cm.
*Filament aspect*.—Straight to slightly undulating.
*Filament color*.—Near RHS Purple-Violet 80C.
Pistil:
*Number*.—Approximately 30 per flower.
*Length*.—Approximately 3 cm.
*Style color*.—Near RHS Yellow 11D.
*Style length*.—Approximately 1.5 cm.
*Stigma*.—Shape: Linear. Color: Near RHS Yellow 11C.

OTHER CHARACTERISTICS

Seeds: Per flower, typically 30 round seeds, approximately 0.15 diameter. Colored near RHS Green 137B.
Disease/pest resistance: Very good resistance to pathogens and pests common to *Clematis* have been observed.
Temperature tolerance: Observed to tolerate temperatures from approximately −5° C. to at least 35° C.

What is claimed is:

1. A new and distinct cultivar of *Clematis* plant named 'UNAI 008' as herein illustrated and described.

* * * * *